United States Patent [19]
Theoharides

[11] Patent Number: 5,821,259
[45] Date of Patent: Oct. 13, 1998

[54] H$_3$-RECEPTOR AGONISTS AS THERAPEUTIC AGENTS

[76] Inventor: Theoharis C. Theoharides, 14 Parkman St., #2, Brookline, Mass. 02146

[21] Appl. No.: 524,023

[22] Filed: Sep. 6, 1995

Related U.S. Application Data

[63] Continuation of Ser. No. 284,041, Aug. 1, 1994, abandoned, which is a continuation of Ser. No. 37,697, Mar. 24, 1993, abandoned, which is a continuation of Ser. No. 790,343, Nov. 12, 1991, abandoned.

[51] Int. Cl.$^6$ .................................................. A61K 31/415
[52] U.S. Cl. ......................... 514/396; 514/397; 514/400
[58] Field of Search .................... 514/396, 397, 514/400

[56] References Cited

U.S. PATENT DOCUMENTS

| | | | |
|---|---|---|---|
| 4,447,443 | 5/1984 | Goldenberg | 424/273 |
| 4,767,778 | 8/1988 | Arrang | 514/397 |

OTHER PUBLICATIONS

Chemical Abstracts AN 1989: 614796, Cohen et al (EP 307172) Sep. 7, 1988.
Arrang et al, Chem Abst. 113(3): 23542u, Jul. 16, 1990, "Preparation of αβ–dimethyl histamine and stereoisomers as Selective histamuric H$_3$ receptor agonists".
Oishi et al "Effects of histamine H$_3$ agonist (R) α Methyl–histamine . . . " J. Neurochem. 52(5): 1388–92, 1989.
Mansfield "The role of antihistamine Therapy in . . . " J. Allergy Clin Immunol. 86: 673–6 (1990 Oct.) *Abstract only*.

*Primary Examiner*—Keith D. MacMillan
*Attorney, Agent, or Firm*—Foley & Lardner

[57] ABSTRACT

The invention provides a method for preventing and alleviating the harmful biological effects of secretion of chemicals from mast cells in the organism of mammals which leads to clinical conditions namely allergy, asthma, arthritis, dermatitis, interstitial cystitis, inflammatory and irritable bowel disease, migraines, multiple sclerosis, scleroderma or systemic sclerosis, ulcerative disease of the gastro-intestinal tract and urticaria, among others. The method consists in administering to said mammals and especially to human beings an amount, effective against said conditions, of an H$_3$ receptor agonist which has inhibitory activity of neurohormonal activation of mast cell secretion.

10 Claims, No Drawings

$H_3$-RECEPTOR AGONISTS AS THERAPEUTIC AGENTS

This application is a continuation of application Ser. No. 08/284,041, filed Aug. 1, 1994 abandoned, which is a continuation of application Ser. No. 08/037,697 filed Mar. 24, 1993, now abandoned; which is a continuation of parent apparent application Ser. No. 07/790,343 filed Nov. 12, 1991, now abandoned.

BACKGROUND OF THE INVENTION

The present invention relates to the use of histamine-3 ($H_3$)-agonists as therapeutic agents with inhibitory activity of neurohormonal activation of mast cell secretion. It also relates to the use of pharmaceutical compositions containing such agonists as active ingredients. More particularly, the present invention pertains to a method of preventing or alleviating in mammals a disease characterized by an abnormally high number of mast cells, increased activation of mast cells or large amounts of mediators secreted therefrom by administering an $H_3$-agonist with inhibitory activity of neurohormonal activation of mast cell secretion.

Histamine is a molecule found in many tissues where it can bind to specific receptors and lead to particular biologic actions. The histamine-1 ($H_1$) receptor is found on vessels, and its activation leads to dilation and oedema; histamine-2 ($H_2$) receptors are found on exocrine glands, such as the parietal cells in the stomach, where their activation leads to gastric acid secretion and ulcers. Recently, an $H_3$ receptor was identified (Schwartz, J-C. Arrang, J. M., Garbarg, M. and Korner, M. Properties and roles of the three subclasses of histamine receptors in brain. *J. Exp. Biol.* 124:203–224, 1986) and seems to be involved in regulation of perivascular nerve activity (Ishikawa, S. and Sperelakis, N. A novel class ($H_3$) of histamine receptors on perivascular nerve terminals. *Nature* 327:158–160, 1987).

Prior art findings relate to the possible action of $H_3$-agonists to inhibit histamine release (Theoharides, T. C. Histamine$_2$ ($H_2$)-receptor antagonists in the treatment of urticaria. *Drugs* 37:345–355, 1989), to decrease bronchoconstriction (Ichinose, M. and Barnes, P. J. Histamine H3-receptors modulate nonadrenergic noncholinergic neural bronchoconstriction in guinea pig in vitro. *Euro. J. Pharmacol.* 174:49–55, 1989), or to increase the resistance of bronchial blood vessels and lower their permeability so that hemorrhagic phenomena due to vascular fragility will not occur (Ichinose, M., Belvisi, M. G. and Barnes, P. J. Histamine H3-receptors inhibit neurogenic microvascular leakage in airways. *J. Appl. Physiol.* 68:21–25, 1990). However, none of these findings lead one to the claims of this invention and a recent review of $H_3$-agonists does not mention any such claims as potential therapeutic prospects (Timmerman, H. Histamine $H_3$ ligands: just pharmacological tools or potential therapeutic agents? *J. Med. Chem.* 33:4–11, 1990).

SUMMARY OF INVENTION

A method of preventing or alleviating in mammals a disease characterized by an abnormally high number of mast cells, increased activation of mast cells or large amount of mediators secreted therefrom which comprises administering a pharmaceutically effective amount of an $H_3$-agonist with inhibitory activity of neurohormonal activation of mast cell secretion.

A method of preventing or alleviating a painful neuroinflammatory process which comprises administering a pharmaceutically effective amount of an $H_3$-agonist with inhibitory activity of neurohormonal activation of mast cell secretion.

DETAILED DESCRIPTION OF THE INVENTION

Scientific progress has led to a better knowledge of the chemical nature of the substances which are at present known under the name of "$H_3$-agonists". It is under this name, and whatever chemical structure, that the substances responsible for the new therapeutic activity claimed will be designated, which substances are identifiable by their inhibitory activity of neurohormonal activation of mast cell secretion as defined by a specific test, which will be given hereafter.

In the context of this disclosure, the following terms shall be defined as follows:

"Degranulation" is henceforth defined as the release of any or all mediators from any or all secretory granules, whether in parallel, differentially or selectively. Relevant examples of such responses are pain and recruitment of inflammatory cells (e.g. leukocytes) from the circulation.

"Therapeutically effective amount" refers to an amount sufficient to produce inhibition of neurohormonal activation of mast cell secretion at a level of inhibition not less than 20% and preferably greater than 70%.

The "$H_3$-agonists" form a class of synthetic compounds, defined by an exclusive property, namely, the inhibition of the synthesis of histamine from histidine and their displacement from specific $H_3$ receptors by the $H_3$-antagonist thioperamide (Arrang, J. M. et al. Highly potent and selective ligands for a new class of $H_3$ of histamine receptor. *Invest. Rad. Suppl.* 23:5130–5132, 1988). $H_3$-agonists bind to the $H_3$ receptor at a concentration less than $10^{-4}M$ (Molar). The synthesis of certain such compounds has been disclosed in Europe (European Patents 214058, Mar. 11, 1987 and 220489, Apr. 21, 1989). Others are available from commercial sources such as Research Biochemicals Incorporated, Natick, Mass. and Calbiochem Corporation, San Diego, Calif. Yet, others can be synthesized according to prior art methods.

Such $H_3$ receptor agonists are histamine derivatives and, more particularly, molecules where a methyl group has substituted the hydrogen atoms at the side chain of histamine and their chiral analogues (stereoisomers), associated with the starred *C, of the histamine structure shown below (FIG. 1) where H could be substituted by at least $CH_2$, $CH_3$, $CO_2H$, F, Cl or any combination thereof.

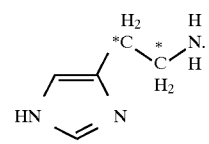

FIG. 1

Illustrative examples of such compounds are the following: R(-)-α-methyl histamine, $N^α$-methyl histamine, $N^τ$-methyl histamine, α-$N^α$-dethylhistamine, α, βdimethyl histamine, $N^α$-methyl-α-(dimethyl)histamine, $N^α$-methyl-α-(chloromethyl)histamine, or α, β-difluro-$N^α$-(fluoromethyl)histamine etc.

I.

MAST CELL BIOLOGY

Mast cells are a normal component of the connective tissue and play an important role in allergy and inflammation. They are localized in the brain, gastrointestinal tract, lung and skin. They are believed to be located there because these tissues are the main entry points for infective organisms and allergens—chemicals which trigger the body's immune response.

Recently, mast cells have been shown to be located at strategic points around capillaries and small blood vessels, especially in the brain, where they are important in regulating the extent of constriction or dilation of the vessels which make up the blood-brain barrier, the protective lining of the brain which excludes toxic materials (Theoharides, T. C. Mast Cells: the immune gate to the brain. *Life Sci.* 46:607–617,1990).

Each mast cell contains up to 500 secretory granules, each storing more than 20 potent biological compounds. Mast cells secrete the contents of theses granules (i.e., degranulate) when triggered by various specific and non-specific mechanisms. Such is the allergic reaction involving immunoglobulin E (IgE) and antigen (Ag) where IgE binds strongly to mast cells through its Fc receptor. When mast cell-bound IgE reacts with an antigen, the latter bridges two or more IgE and causes mast cell degranulation with subsequent release of mediators, either stored or synthesized during degranulation. Other known triggers include the neurotransmitter acetylcholine, various neuropeptides such as caldtonin-gene-related peptide (CGRP), neurotensin, substance P, somatostatin and vasoactive intestinal peptide (VIP), viruses, bacterial toxins, drugs, such as aspirin, morphine and curare, contrast media used in radiology, extreme heat, cold, solar radiation, hyperosmotic media and pressure.

The degranulation of mast cells in response to various agents is a biological consequence of the activation of one or more receptors which are located on the surface of the mast cell. The best known receptor is IgE, which is involved in allergic reactions—the only pathological process documented to involve mast cells to date. However, there has been recent evidence that neurotransmitters such as acetylcholine, and neuropeptides, molecules released from neurons in the peripheral and central nervous systems (brain), may also trigger mast cell degranulation through specific receptors, especially in response to stress. Such neuropeptides include calcitonin gene related peptide (CGRP), neurotensin (NT), peptide Y, somatostatin (SRIF), substance P (SP) and vasoactive intestinal peptide (VIP) among others (Theoharides, T. C. Mast cells: the immune gate to the brain. *Life Sci.* 46:607–617,1990), as well as female sex hormones (Vliagoftis, H. et al. Progesterone triggers selective mast cell secretion of 5-hydroxytryptamine. *Int. Arch. Allergy Appl. Immunol.* 93:113–119, 1990). It is, therefore, clearly important to block mast cell degranulation in response to any such stimulus.

The compounds released by the mast cells following degranulation are known to cause many biological responses which are part of the overall response of the body to invasion by infective organisms (inflammatory response) or allergens.

Compounds released by mast cell degranulation may be: histamine, kinins, prostaglandin $D_2$ and vasoactive intestinal peptide, which are vasodilatory, as well as serotonin, prostaglandin $F_{2\alpha}$. and leukotrienes, which are vasoconstrictive. In addition, histamine and kinins and prostaglandins can cause pain directly, and enzymes which destroy proteins and phospholipids can cause tissue damage directly.

Table 1 indicates the numerous chemicals stored and released from mast cells.

TABLE 1

Mast Cell Mediators

| Prestored | De Novo |
|---|---|
| Arylsulfatases | Leukotrienes $LTB_4$ |
| Chemotactic factors | Leukotrienes |
| Chymase | Platelet Activation factor(PAF) |
| Cytokines (IL-1,2,3,4,5 & 6, GM-CSF, TNF) | Prostaglandins |
| | Thromboxanes |
| Heparin | |
| Histamine | |
| Kinogenases | |
| Serotonin | |
| Tryptase | |

Histamine and the other mediators are secreted from the granules of mast cells during degranulation. The histamine and other mediators then bind to specific receptors on the surface of endothelial cells on vessels, neurons or other tissues. Vasodilation and chemoattraction permits lymphocytes to leave the blood circulation and enter the tissue, where they cause additional mast cell degranulation and other responses. The process of degranulation continues, eventually involving many mast cells. It is important to note that anti-histamines act only after the initial release of histamine. They do not block either the secretion of other mediators or the action of any other mediators.

Mast cells are known to be necessary for the establishment of immediate hypersensitivity reactions, (e.g. allergy, anaphylaxis). However, recent evidence indicates that they are also necessary for delayed hypersensitivity reactions (the delayed response) which is required for inflammation to occur. It is believed that mast cell chemicals such as histamine and prostaglandins dilate local vessels permitting blood-borne leukocytes to enter the affected organ and create the inflammation, leading to tissue destruction and fibrotic changes. Secondary reactions from mast cell and leukocyte chemicals, along with the tissue destruction itself, cause the pain associated with these conditions. Table 2 lists endogenous pain-producing substances released from mast cells.

TABLE 2

Endogenous Pain-Producing Chemicals Secreted From Mast Cells

Adenosine phosphates (AAP, ADP, ATP)
Bradykinin
Histamine
5-Hydroxytryptamine (serotonin)
Leukotrienes
Lymphokines
Potassium
Prostagladins
Tumor necrosis factor

NEURONAL AND MAST CELL SECRETION INHIBITORY ACTIVITY OF H-3 AGONISTS

Compounds which have inhibitory activity of neurohormonal activation of mast cell secretion can be tested by preincubating mast cells purified from the peritoneal cavity of rats with various concentrations of $H_3$-agonists, typically 0.1 $\mu$mol/L to 1,000 $\mu$mol/L, for various times at 37° C. before stimulating mast cell secretion with a stimulus such as somatostatin (Theoharides, T. C. and Douglas, W. W. Somatostatin induces histamine secretion from rat peritoneal mast cells. *Endocrinology* 102:1637–1640, 1978).

More appropriate to neuroinflammatory diseases, compounds which have inhibitory activity of neurohormonal activation of mast cell secretion can be tested by preincubating brain mast cells and neurons before triggering them to secrete in situ using slices of rodent brains in perfusion chambers and measuring secreted chemicals (Lambracht-Hall, M., Konstantinidou, A. D. and Theoharides, T. C. Serotonin release from brain mast cells in vitro. *Neuroscience* 39:199–207, 1990). Moreover, compounds which have inhibitory activity of neurohormonal activation of mast cell secretion can be tested by treating rats intravenously before triggering perivascular mast cells by direct nerve stimulation (Dimitriadou, V., Buzzi, M. G., Moskowitz, M. A. and Theoharides, T. C. Trigeminal sensory fiber stimulation induces morphologic changes reflecting secretion in rat dura mater mast cells. *Neuroscience* 44:97–112, 1991).

The ability of $H_3$-agonists to inhibit neurohormonal activation of mast cell secretion has been and can be documented in all three types of assays. All of the clinical conditions listed below occur more frequently in females than in males and it is claimed that $H_3$-agonists are particularly effective in having inhibitory activity of neurohormonal activation of mast cell secretion against neurohormonal triggers of mast cell secretion, such as neuropeptides and female sex hormones, such action being determined by the aforementioned tests.

The mechanism of action of $H_3$-agonists is at least two fold:

a. They inhibit neuronal secretion of chemicals (e.g. neurotransmitters, neuropeptides, neurohormones) which trigger mast cells and b. they inhibit mast cell secretion irrespective of the trigger.

III.

THERAPEUTIC INDICATIONS

1. Allergy. This condition is characterized by excessive stimulation of mast cells in various tissues, especially the lungs, nasal mucosa and skin. Stimulation is often due to seasonal allergic triggers, such as pollen, and the only pharmacological agents used are antihistamines which block the action of histamine, only one of the many mediators released from mast cells.

2. Asthma. This condition is characterized by excessive stimulation of mast cells in the airways, sometimes by allergens such as pollen, and others by internal factors such as hormones or stress. The pharmacological agents used are methylxanthines (theophylline, aminophylline), $\beta_2$-adrenergic agonists (terbutaline) to dilate the bronchi, as well as steroids (beclomethasone) and disodium cromoglycate (cromolyn) to stabilize immune cells and mast cells, respectively.

3. Arthritis. This condition is characterized by an inflammation of the peripheral joints where leukocytes enter after leaving the blood circulation and release chemicals which are destructive to the joint, cause pain directly and recruit more destructive cells into the inflamed area. Mast cells have recently been found in inflamed joints and they are activated by neuropeptides secreted in the synovium. A variety of drugs have been used in this condition, primarily nonsteroidal anti-inflammatory drugs, such as salicylates, indomethacin, ibuprofen, naproxen, fenoprofen, tolmetin, sulidac, medofenamate, ketoprofen, piroxicam, dipyrone and didofenac. Other drugs which have been used include gold compounds, d-penicillamine, hydroxdoroquine, corticosteroids, and immunosuppressive drugs, such as cyclophosphamide, methotrexate and azathioprine. However, all these drugs reduce the symptoms to various degrees, but fail to address the cause or prevent recurrences.

4. Dermatitis (eczema). This condition is characterized by the action of various noxious substances during which skin mast cells are activated and secret chemicals which may lead to chronic inflammatory changes, fibrosis and pain. The only drugs used are creams containing steroids, such as hydrocortisone.

5. Interstitial cystitis (IC). IC is a urologic condition of unknown etiology that predominantly affects young and middle-aged females with a prevalence of 5 times higher in women than men and for which there is no effective therapy and may represent the end-organ response on the part of the human bladder to diverse, heterogenous stimuli. IC is characterized by irritative voiding symptoms (frequency, nocturia) and suprapubic or pelvic pain related to and relieved by voiding; dyspareunia is also common.

The role of the mast cell in the bladder wall has recently acquired significance since it was shown that mast cells may be activated without an increase in their numbers (Theoharides, T. C. and Sant, G. R. Bladder mast cell activation in interstitial cystitis. *Sem. Urology* 9:74–87, 1991). intravesicular administration of pentosan polysulfate and dimethylsulfoxide has been tried to treat IC with little success. There still is no effective treatment.

6. Inflammatory and irritable bowel disease (IBD). This term is used to describe a spectrum of gastrointestinal inflammation such as Crohn's disease, as well as various forms of infectious diarrhea, such as that due to *Clostridium difficile*. The prevalence of irritable bowel disease is 20 times higher in women than in men. Recent evidence indicates that mast cells exist in the mucosa of the small intestine and that they are different from mast cells in other, especially connective tissues. Moreover, they have also been shown to be in dose apposition to nerve endings, suggesting that they may be affected by the nervous system.

The only available therapy for non-infectious forms of colitis is anti-inflammatory steroids and 5-aminosalicylic acid analogues, neither of which is effective. In addition, IBD is treated with anticholinergics or agents which lower intestinal motility such as diphenoxylate, loperamide, opium tincture or codeine. Corticosteroid therapy has been used in the acute stages of Crohn's Disease, while immunosuppressive drugs including 6-mercaptopurine, cyclosporin A and azathioprine has also been used without apparent benefit.

7. Migraines. Migraine headaches are known to produce the most intense headaches reported, which are comparable to that of a brain aneurysm rupture. As many as 15% of all people, especially in industrialized societies, are sufferers. There is no way known to the art to effectively prevent the migraine headache. The pathophysiology of migraine headaches appears to involve a variety of stimuli (intense light, noise, anxiety, exertion, cold, heat, hormones, food additives, certain foods) which result in constriction of extracranial vessels. This subsequently spreads to intracranial vessels resulting in brain anoxia (lack of oxygen,). The vasoconstriction is followed by a sequential or reflex powerful vasodilation, and it is during this phase that a patient feels an intense throbbing headache. Increased levels of norepinephrine, serotonin and products of tissue anoxia are considered to be the endogenous pain producing molecules accompanied by direct sensory nerve stimulation, because of stretching due to vasoconstriction and vasodilation. Vasoconstriction is the closing or tightening of the arteries, which reduces blood flow; vasodilation is the opening of the vessels to increase blood flow, while bronchoconstriction is bronchial muscle contraction.

Mast cells are located around the cranial vessels involved in the pathophysiology of migraines and are known to be activated and release their chemicals by neuropeptides and female sex hormones. Compounds released by mast cell degranulation which may be associated with migraines include: histamine, kinins and prostaglandin $E_2$ and vasoactive intestinal peptides, which are vasodilatory, as well as serotonin, prostaglandin $F_{2\alpha}$ and leukotrienes, which are vasoconstrictive. In addition, histamine, kinins, prostaglandins and serotonin can cause pain directly.

The prior art suggest that symptomatic treatment (after the attack) of migraine headaches can be achieved through use of extracranial vasoconstrictors, typically ergot alkaloids such as ergotamine, or 5-hydroxytryptamine (5-HT, serotonin) agonists such as sumatriptan, while prophylactic treatment involves serotonin antagonists such as methysergide and cyproheptadine, beta-adrenergic blockers, such as propranolol, nadolol, timolol or atenolol; tricyclic anti-depressants, such as amitriptyline; calcium channel antagonists, such as verapamil and phenothiazines, such as meclizine or phenelzine. However, these drugs, such as propranolol, verapamil or amitriptyline have severe side effects because the first two inhibit the function of the heart, the last causes a drop in blood pressure, and all three can cause impotence. Moreover, if vasoconstrictors or serotonin agonists are taken before the migraine, they may precipitate the migraine. Opioid analgesics, such as morphine, are known to make the migraine worse and so do non-opioid analgesics, such as aspirin, ibuprofen and the like, because at high concentrations, they activate mast cells.

The reported use, if any, of anti-histamines, such as hydroxyzine, seems to have been limited to the alleviation of some symptoms of migraine headache (nausea) after the symptom has appeared, but not the pain or the underlying condition itself.

8. Multiple sclerosis (MS). MS is one of the most common neurologic diseases in North America and Europe. It is a chronic demyelinating disease of the central nervous system, affecting approximately 250,000 Americans with 4 times higher prevalence in women. The disease is manifested in the nervous system by inflammation and primary demyelination, i.e. breakdown of the insulating material (myelin) around a nerve axon (the electrical "wires" carrying messages from the brain), which results in retarded nerve conduction leading to incoordination, paralysis and death.

The loss of myelin in MS results from an inflammatory reaction mediated by cells, primarily macrophages and T-lymphocytes, which are derived from the peripheral circulation and which migrate across blood vessels and into the brain. The antigen or target of the inflammatory reaction is not known, although it is assumed that it must be a component of myelin. Abnormal levels of mast cells have been found in the brains of persons afflicted with MS and it has been proposed that mast cells alter the protective blood-brain barrier, thus permitting the entry of inflammatory cells which destroy myelin (Theoharides, T.C. *Life Sci.* 46:607–617, 1990).

Most therapeutic trials in MS have attempted to nonspecifically suppress or dampen the immune response by destroying or inactivating cells of the immune system with either corticosteroids or immunosuppressants such as cyclophosphamide. There is no specific therapy for the treatment of disease.

9. Neurofibromatosis. Neurofibromatosis, sometimes called Recklinhauser's disease, is a neurodermatologic disease of unknown etiology which occurs at least three times as often in women than in men. It is characterized by numerous small tumors of the skin which involve peripheral nerves with associated fibrotic changes of the skin. This condition involves pain and can result in disfiguration. Mast cells have often been see in association with these skin tumors. There is no effective therapy for this condition.

10. Osteoporosis. Rapid bone loss is known to occur after menopause when estrogen rapidly declines and is associated with increased incidence of fractures. In ovariectomized mature rats, a significant correlation was reported following surgery, between large mast cells and trabecular bone volume and between mast cell density and the percent erosion surface. During an investigation of the bone response to calcium deficient diets over time, dramatic increases in the numbers of mast cells were observed in the metaphyseal region of tibia, which showed osteitis fibrosa, and eventually net loss of bone. Treatment with vitamin D, but not parathyroid hormone extract, reversed the induced bone defect and the number of mast cells decreased. It was speculated that the loss of bone might be correlated with the increased numbers of mast cells lying close to the trabecular surface of metaphyseal bone. The progression of osteoporosis may be slowed down by drugs such as etidronate and the natural hormone, calcitonin. In face, mast cell secretion was shown to be stimulated by parathyroid hormone (PTH) in vitro. There have been several recent case reports of osteoporosis associated with systemic mastocytosis, an uncommon disorder of mast cells. In some cases, osteoporosis was the sole presentation of bone marrow mastocytosis.

11. Psoriasis. This is an autoimmune condition characterized by inappropriate proliferation of skin cells which are associated with excessive stimulation of local mast cells leading to itching. Creams containing steroids, such as hydrocortisone, and the immunosuppressive agent methotrexate have been used without much success.

12. Scleroderma or systemic sclerosis. Scleroderma is an autoimmune disease which occurs five times more often in women than men. It involves the whole body, but it primarily manifests itself on the skin which is progressively replaced by fibrotic tissue giving a hardened and aged appearance. Other peripheral manifestations are Raynaud's phenomenon, which is characterized by intense vasoconstriction of the hand vessels leading to anoxia and pain. Mast cells have often been associated with these fibrotic skin changes. There is no effective therapy for this condition even though calcium entry blockers such as nifedipine and verapamil have been used.

13. Systemic mastocytosis. This is a condition characterized by either increased number of mast cells and/or excessive activation of mast cells in many different organs leading to a number of symptoms including allergy, asthma, diarrhea, flushing of the face, headaches and cardiovascular problems. There is no effective therapy for this condition.

14. Ulcerative disease of the gastro-intestinal tract. In this condition, local stomach mast cells are activated by the neurotransmitter acetylcholine, hormones, drugs, pressure and stress to release histamine which then stimulates the parietal cells of the stomach to release gastric acid. The excess acid causes ulceration of the gastrointestinal mucosa. Effective therapy involves histamine-2-receptor antagonists such as cimetidine or ranitidine and antacids which neutralize the acidity of the gastric juice.

15. Urticaria. This condition is characterized by excessive stimulation of skin mast cells by exogenous (allergens) and endogenous (stress) factors leading to intense itching often associated with angioedema. Histamine-1-receptor antagonists, such as hydroxyzine, have been used with variable success.

IV.

PREFERRED EMBODIMENT

In accordance with the present invention, $H_3$-agonists may be administered to patients suffering from migraines in any conventional oral or parenteral dosage form. Oral dosage forms may include tablets, capsules, caplets, liquids and the like, including generally from about 50 to about 250 mg of $H_3$-agonists per dosage unit together with suitable pharmaceutically acceptable excipients, binders, sweeteners, coloring agents and other conventional additives. Parenteral dosage forms may include any conventional injectable solutions of $H_3$-agonists, as for example, an isotonic saline solution together with pharmaceutically acceptable preservatives and buffers. The parental dosage forms generally contain from about 50 to about 250 mg of $H_3$-agonists and may be injected by the subcutaneous, intramuscular, intravenous or intravesical routes.

By one preferred method, the $H_3$-agonists may be initially administered to patients in two daily doses of 100 or 200 mg each, with gradual increments of 100 or 200 mg twice per day up to a maximum of 2,500 mg twice per day.

For example, the method of the present invention consists of the daily administration to patients suffering from migraines of from about 0.1 mg to about 5,000 mg per Kg body weight of $R(-)-\alpha$-methylhistamine. The oral route of administration is preferred so that the patient can self-medicate.

The method of the present invention could provide dramatic symptomatic relief for patients suffering from migraines even where conventional modalities of treatment have failed. Patients receiving $R(-)-\alpha$-methylhistamine treatment will experience a decrease in painful symptoms and will be able to carry on their daily activities in a relatively normal fashion in comparison with their pre-treatment state.

EXAMPLE

Male Sprague/Dawley rats, weighing approximately 300 grams, were obtained from Taconic Labs (Germantown, N.Y.) and their brains were removed after decapitation during ether anesthesia. Brain slices were incubated with radiolabelled 5-hydroxytryptamine (serotonin), $^3$H-5-HT (New England Nuclear, Mass.) which was taken up by brain mast cells and neurons. After washing, these brain slices were stimulated in a custom-made perfusion chamber with either a) 100 µg/ml of compound 48/80 which specifically activates brain mast cell secretion or b) 40 mM potassium which specifically activates brain neuron secretion. In either case, activation results in secretion of radiolabelled serotonin which is used as an index of activation. Serotonin secreted from these two cell sources is believed to be involved in the pathophysiology of migraines; inhibition of serotonin secretion would, therefore, constitute the therapeutic equivalent of its use in humans suffering from migraines. Pretreatment of these brain slices with $10^{-6}$M (Molar) of the $H_3$-agonist $R(-)-\alpha$-methylhistamine (Research Biochemicals Incorporated, Natick, Mass.) inhibited both brain mast cell and neuronal secretion of serotonin by more than 70%. This is the first instance ever where stimulation of brain serotonin secretion by triggers specific for both mast cells and neurons is inhibited by an $H_3$-agonist and leads one directly to the therapeutic application of $H_3$-agonists to the treatment of migraines.

The invention being thus described, it will be obvious that the same may be varied in many ways. Such variations are not to be regarded as a departure from the spirit and scope of the invention, and all such modifications are intended to be included within the scope of the claims.

What is claimed is:

1. A method of treating a migraine headache in a patient, comprising administering to said patient a pharmaceutically effective amount of an histamine $H_3$-receptor agonist.

2. The method of claim 1, in which the $H_3$-agonist is α, β-difluro-$N^\alpha$-(fluoromethyl)histamine.

3. The method of claim 2, in which the α, β-difluro-$N^\alpha$ (fluoromethyl)histamine is used as a pharmaceutically acceptable salt.

4. The method of claim 1, in which the pharmaceutically effective amount is from about 0.01 mg/kg to 5,000 mg/kg body weight.

5. A method according to claim 1, in which the $H_3$receptor-agonist is administered to the patient in an oral dosage form comprising a dispersible powder, a tablet, a capsule, a liquid, a semiliquid suspension or a slow release formulation.

6. A method according to claim 1 in which the $H_3$receptor-agonist is administered to the patient parenterally.

7. A method according to claim 6 in which the $H_3$receptor-agonist is administered to the patient by the subcutaneous, intramuscular, intravenous, intravesical, transmucosal or transdermal routes.

8. A method according to claim 4 in which the effective amount is from about 0.05 mg to 1,000 mg/kg body wt.

9. A method according to claim 1, wherein said migraine results from at least one chemical released from dural mast cells wherein said chemical is selected from the group consisting of ATP, bradykinin, nitric oxide, prostaglandin $D_3$, tryptase, Tumor Necrosis Factor, and Vasoactive Intestinal Peptide.

10. The method of claim 1, wherein said $H_3$-receptor agonist is selected from the group consisting of $N^\alpha$-methyl histamine, α-$N^\alpha$-dimethyl histamine, $N^\alpha$-methyl-α-(dimethyl) histamine and α, β-difluoro-$N^\alpha$(fluoromethyl) histamine.

* * * * *